United States Patent [19]

Evans

[11] 4,391,815

[45] Jul. 5, 1983

[54] CYANOBENZANO[B]PYRANS

[75] Inventor: John M. Evans, Royden, England

[73] Assignee: Beecham Group Limited, England

[21] Appl. No.: 198,280

[22] Filed: Oct. 17, 1980

Related U.S. Application Data

[60] Continuation-in-part of Ser. No. 79,560, Sep. 27, 1979, abandoned, and Ser. No. 117,261, Jan. 31, 1980, abandoned, which is a division of Ser. No. 970,199, Dec. 18, 1978, Pat. No. 4,251,537, which is a continuation of Ser. No. 776,976, Mar. 14, 1977, abandoned.

[30] Foreign Application Priority Data

| Apr. 2, 1976 | [GB] | United Kingdom | 13536/76 |
| Apr. 10, 1976 | [GB] | United Kingdom | 33178/76 |
| Oct. 4, 1978 | [GB] | United Kingdom | 39303/78 |
| Oct. 20, 1978 | [GB] | United Kingdom | 41306/78 |
| Jan. 10, 1979 | [GB] | United Kingdom | 7900901 |

[51] Int. Cl.³ .................. A61K 31/395; C07D 405/04
[52] U.S. Cl. .................................... 424/274; 424/278; 424/267; 546/196; 548/525; 549/399
[58] Field of Search ............... 546/196; 260/326.34, 260/326.5 D, 345.2; 424/267, 274, 278; 549/399

[56] References Cited

U.S. PATENT DOCUMENTS 4,048,317  9/1977  Watts .................................. 546/196

FOREIGN PATENT DOCUMENTS 1548221  7/1979  United Kingdom ................ 546/399

Primary Examiner—Robert T. Bond
Attorney, Agent, or Firm—Jacobs & Jacobs

[57] ABSTRACT 2,2-Dimethyl-3,4-dihydro-2H-benzo[b]pyran-3-ols bearing an amino group in the 4-position and a cyano group in the benzo ring, their salts, esters and ethers, demonstrate excellent vasodilatory activity. The compounds, of which trans-2,2-dimethyl-4-isopropylamino-6-cyano-3,4-dihydro-2H-benzo[b]pyran-3-ol is a representative embodiment, can be prepared from the corresponding 3,4-epoxy derivative upon treatment with an amine.

14 Claims, No Drawings

CYANOBENZANO[B]PYRANS

CROSS-REFERENCE

This is a continuation-in-part of Ser. No. 079,560 filed Sept. 27, 1979, now abandoned; and Ser. No. 117,261, filed Jan. 31, 1980, now abandoned which, in turn, is a divisional of Ser. No. 970,199 filed Dec. 18, 1978, now U.S. Pat. No. 4,251,537, which in turn is a continuation of Ser. No. 776,976, filed Mar. 14, 1977, now abandoned.

DETAILED DESCRIPTION

This invention relates to cyano substituted benzo[b]-pyrans which are useful as intermediates and in the treatment of hypertension.

Accordingly the present invention provides cyano-benzo[b]-pyrans of the formula (I):

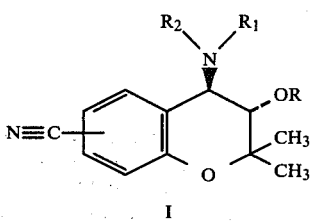

and the pharmaceutically acceptable acid addition salts thereof, wherein $NR_1R_2$ is alkylamino of 1 to 4 carbon atoms, pyrrolidino or piperidino and R is hydrogen, alkyl of 1 to 3 carbon atoms, alkanoyl of up to 8 carbon atoms or benzoyl.

As illustrated in the formula (I), the $-N(R_1)(R_2)$ and -OR moieties are trans.

Examples of such cyano compounds of Formula (I) include:
trans-2,2-dimethyl-4-piperidino-6-cyano-3,4-dihydro-2H-benzo[b]pyran-3-ol, and its hydrochloric salt;
trans-2,2-dimethyl-4-pyrrolidino-6-cyano-3,4-dihydro-2H-benzo[b]pyran-3-ol, and its hydrochloric salt;
trans-2,2-dimethyl-4-isopropylamino-6-cyano-3,4-dihydro-2H-benzo[b]pyran-3-ol, and its hydrochloric salt;
trans-2,2-dimethyl-3-methoxy-4-pyrrolidino-6-cyano-3,4-dihydro-2H-benzo[b]pyran; and
trans-2,2-dimethyl-3-(2,2-dimethylpropanoyloxy)-4-pyrrolidino-6-cyano-3,4-dihydro-2H-benzo[b]pyran.

The compounds of the Formula I have excellent vasodilatory activity. In particular the compounds demonstrate a favorable therapeutic ratio; i.e., the separation of desired vasodilatory effects from undesired cardiac effects.

R can be hydrogen, methyl, ethyl, n-propyl or isopropyl, of which methyl is preferred. R can also be an unsubstituted carboxylic acyl group such as acetyl or propionyl, or benzoyl. Preferably R is a hydrogen atom. Moreover the cyano group is preferably in the 6-position.

It will be appreciated that the depicted trans isomer can exist in the form of a mixture of stereoisomers or as a single stereoisomer. It is particularly convenient to prepare the compounds as racemic mixtures. Most of the desired biological activity is found in the (+)-isomer of the compound wherein R is hydrogen and in the derivatives thereof wherein R is alkyl or acyl. Thus in a preferred aspect this invention provides such (+)-isomer. Racemic mixtures can be separated into pure optical isomers using such techniques as fractional crystallization of salts with optionally active acids.

Suitable acid addition salts of the compounds of the Formula I are those with pharmaceutically acceptable inorganic or organic acids such a hydrochloric, hydrobromic, phosphoric, sulphuric, methanesulphonic, toluenesulphonic, acetic, propionic, succinic, citric, tartaric, mandelic, lactic, gluconic or the like acid.

The compositions of this invention are most suitably adapted for oral administration, although other modes of administration such as by injection, for example by intravenous injection for heart failure, are also suitable.

In order to obtain consistency of administration it is preferred that the compositions of this invention are in the form of a unit-dose. Suitable unit dose forms include tablets, capsules and other powders in sachets or vials. Unit dose forms generally will contain from 1 to 100 mg of the compound and more usually from 2 to 50 mg, for example 5 to 25 mg; e.g., 6, 10, 15 or 20 mg. Such compositions may be administered from 1 to 6 times a day, more usually from 2 to 4 times a day, in a manner such that the daily dose is from 5 to 200 mg for a 70 kg human adult and more commonly from 10 to 100 mg.

Shaped oral dosage compositions are favored composition aspects.

In addition such compositions may contain further active agents such as other anti-hypertensive agents, diuretics and β-blocking agents. β-blocking agents are particularly suitable for inclusion in the compositions of this invention. For example, propranolol may be included in conventionally used quantities.

The compositions of this invention are formulated in conventional fashion, as for example in a manner similar to that used for known antihypertensive agents such as hydrallazine.

Oral dosage forms may contain such conventional agents as fillers (diluents), lubricants, binders, disintegrants, colourants, flavourings, surface active agents, preservatives, buffering agents and the like. Typical fillers include microcrystalline cellulose, manitol, lactose and other similar agents. Suitable disintegrants include starch, polyvinylpyrrolidone and starch derivatives such as sodium starch glycollate and the like. Typical lubricants include stearic acid, magnesium stearate, magnesium lauryl sulphate and similar agents. The oral compositions can be prepared by conventional methods of blending, filling, tabletting and the like. Repeated blending operations can be used to distribute the active ingredient throughout those compositions containing large quantities of fillers, as is conventional.

Oral compositions normally will be used in the treatment of chronic hypertension rather than acute. For emergency use, for example in heart failure cases, intravenous administration may be indicated. Intravenously administrable sterile solutions in water for injection can be made up from the sterile composition in a vial in accordance with conventional practice.

The hypotensive activity of the compounds of the present invention can be conveniently observed in conventional animal models, of which the following is representative:

Systolic blood pressures are determined by a modification of the tail cuff method described by Claxton et al., *European Journal of Pharmacology*, 37, 179 (1976). An oscilloscope (or W+W BP recorder, model 8002) can be used to display pulses. Prior to all measurements rats are placed in a heated environment (33.5°±0.5° C.)

before transfer to a restraining cage. Each determination of blood pressure is the mean of at least 6 readings.

Typical results are as follows [in which due to animal availability spontaneously hypertensive rats (ages 12–18 weeks, systolic blood pressures >170 mm Hg) were used in the Compound A tests, and DOCA-salt treated hypertensive rats were used in the Compound B and C tests]:

TABLE I

| Com- pound | Dose mg/kg p.o. | No. of Animals | Initial B.P. mm Hg | % Change in B.P. (Systolic) | | | | |
|---|---|---|---|---|---|---|---|---|
| | | | | 1 hr. | 2 hr. | 4 hr. | 6 hr. | 24 hr. |
| A | 1 | 5 | 208 ± 3 | −22 ± 2 | −21 ± 2 | −29 ± 2 | −21 ± 2 | −18 ± 2 |
| A | 0.3 | 6 | 197 ± 2 | −21 ± 2 | −12 ± 2 | −8 ± 2 | −2 ± 2 | +6 ± 4 |
| B | 1 | 5 | 185 ± 88 | −3 ± 3 | −4 ± 3 | −5 ± 3 | −1 ± 2 | +9 ± 1 |
| C | 1 | 6 | 191 ± 4 | −37 ± 2 | −27 ± 3 | −23 ± 4 | −14 ± 3 | +4 ± 3 |
| Com- pound | Dose mg/kg p.o. | No. of Animals | Initial Heart Rate | % Change in Heart Rate | | | | |
| | | | | 1 hr. | 2 hr. | 4 hr. | 6 hr. | 24 hr. |
| A | 1 | 5 | 471 ± 11 | +10 ± 3 | +8 ± 2 | +7 ± 2 | +7 ± 2 | −4 ± 4 |
| A | 0.3 | 6 | 477 ± 5 | +2 ± 1 | −8 ± 2 | −6 ± 1 | −4 ± 1 | −4 ± 4 |
| B | 1 | 5 | 344 ± 17 | +16 ± 7 | +10 ± 7 | +2 ± 6 | +2 ± 2 | +17 ± 6 |
| C | 1 | 6 | 331 ± 13 | +22 ± 3 | +17 ± 5 | +7 ± 6 | +13 ± 4 | +9 ± 3 |

The compounds identified as A, B and C are as follows:
A = trans-2,2-dimethyl-4-pyrrolidino-6-cyano-3,4-dihydro-2H-benzo[b]pyran-3-ol HCl.
B = (−)-trans-2,2-dimethyl-4-pyrrolidino-6-cyano-3,4-dihydro-2H-benzo[b]pyran-3ol HCl.
C = (+)-trans-2,2-dimethyl-4-pyrrolidino-3,4-dihydro-2H-benzo[b]pyran-3-ol HCl.

The compounds of the invention can be prepared by allowing a compound of the formula (II):

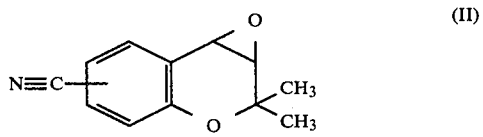

to react with an amine of the formula H—N(R$_1$)(R$_2$) to produce a compound of the Formula I wherein R is hydrogen. The reaction can be carried out at any non-extreme low, medium or high temperature, as for example from −10° C. to 200° C. In general ambient or slightly elevated temperatures are most suitable, as for example, 12° to 100° C. The reaction is normally carried out in a solvent such as a lower alcohol or lower ketone, as for example methanol, ethanol, propanol, acetone or methylethylketone. It has been found that the reaction proceeds smoothly if carried out in refluxing ethanol. The compound of the formula II can be prepared in situ, for example from a corresponding bromohydrin.

The product, which is the trans form, can be obtained from the reaction mixture by removal of the solvent, normally accomplished by evaporation under reduced pressure. The initial product may contain some epoxide, which can be separated by dissolving the reaction product in ethyl acetate and extracting with dilute acid. If desired the solvent may be evaporated at this stage but it is usually more convenient to render the mixture basic, back extract with ethyl acetate and recover by evaporation at reduced pressure. If a salt is desired, this product which is the free base may be dissolved in diethyl ether containing a little ethanol and treated with a solution of the acid, for example in diethyl ether. The desired salt can then be collected by filtration.

Etherification of the initially produced compound (R=hydrogen) can be effected in a conventional manner, as for example the reaction with alkyl iodide in the presence of a base such as potassium tert-butoxide in an inert solvent such as toluene.

Preparation of esters (R=alkanoyl or benzoyl) can be effected by conventional methods of esterification such as the reaction with an acylating agent, optionally in the presence of an acid acceptor. Suitable acylating agents include acid halides such as bromide or chloride, an acid in the presence of a condensation promoting agent such as dicyclohexylcarbodiimide or its chemical equivalent, and acid anhydrides. Such reactions are generally carried out in a non-hydroxylic solvent at a non-extreme temperature.

The following examples will serve to further illustrate the invention:

EXAMPLE 1

Trans-2,2-dimethyl-4-piperidino-6-cyano-3,4-dihydro-2H-benzo[b]pyran-3-ol

4-Cyanophenol (19.6 g), sodium hydroxide pellets (9.9 g), 3-chloro-3-methylbut-1-yne (40.85 g) and benzyltrimethylammonium hydroxide (34.5 g, 40% in methanol) were stirred in methylene chloride (150 ml) and water (150 ml) at room temperature for 4 days. After separation of the layers, the aqueous layer was extracted twice with chloroform. The combined organic extracts were evaporated and the residue taken up in ether and washed with water and 2 N sodium hydroxide solution before drying over anhydrous sodium sulphate. Removal of solvent and drying agent gave an oil (15.72 g). Distillation at 0.5 mm Hg gave the analytic material as the fraction boiling at 96°–102° C. (10.13 g).

Cyclisation of the 3-(p-cyanophenoxy)-3-methylbut-1-yne (9.77 g) was accomplished by heating in diethylaniline at 210°–220° C. under nitrogen. Purification by distillation, and extraction with dilute hydrochloric acid gave 2,2-dimethyl-6-cyano-2H-benzo[b]pyran as a colourless oil (6.84 g), which slowly crystallised on standing, having a nmr spectrum showing signals at δ146, 6.25 (d, J=10), 5.67 (d, J=10), 6.74 (d, J=8), 7.18 (d, J=2), 7.34 (q, J=8,2).

To a stirred cooled solution of 2,2-dimethyl-6-cyano-2H-benzo[b]pyran (6.56 g) in dimethyl sulphoxide (65 ml) and water (1.30 ml) was added freshly crystallized N-bromosuccinimide (12.63 g) in one portion. Dilution with water after stirring for an additional 1 hour, and isolation via ethyl acetate gave trans-2,2-dimethyl-3- bromo-6-cyano-3,4-dihydro-2H-benzo[b]pyran-4-ol as a white crystalline solid (10.54 g), a small portion of which recrystallised from 60-80 petroleum ether had m.p. 128°-128.5° C.

This bromohydrin (5.63 g) was stirred with sodium hydroxide (0.80 g) in dioxan (75 ml) and water (18 ml) at room temperature for 3 hours. Work up by dilution and extraction with ethyl acetate gave 2,2-dimethyl-3,4-epoxy-6-cyano-3,4-dihydro-2H-benzo[b]pyran (4.35 g) as a colourless oil having signals at δ1.26 and 1.54 (—CH$_3$), 3.80 (d, J=4, H-4), 3.40 (d, J=4, H-3), 6.77 (d, J=8, H-8), 7.43 (q, J=8.2, H-7) and 7.58 (d, J=2, H-5) in its nmr spectrum.

Treatment of 2,2-dimethyl-3,4-epoxy-6-cyano-3,4-dihydro-2H-benzo[b]pyran (2.09 g) with piperidine (0.86 g) in refluxing ethanol (60 ml) for 24 hours followed by evaporation of solvent gave a yellow oil which was dissolved in the minimum quantity of ethanol and treated with ethereal hydrogen chloride to give crystals of trans-2,2-dimethyl-4-piperidino-6-cyano-3,4-dihydro-2H-benzo[b]pyran-3-ol hydrochloride on standing (2.06 g) of m.p. 253°-257° C.

EXAMPLE 2

Trans-2,2-dimethyl-4-isopropylamino-6-cyano-3,4-dihydro-2H-benzo[b]pyran-3-ol

By substituting an equivalent amount of isopropylamino for piperidine in the procedure of Example 1, there was obtained trans-2,2-dimethyl-4-isopropylamino-6-cyano-3-4,dihydro-2H-benzo[b]pyran-3-ol, m.p. 251° C.

EXAMPLE 3

Trans-2,2-dimethyl-4-pyrrolidino-6-cyano-3,4-dihydro-2H-benzo[b]pyran-3-ol

4-Cyanophenol (19.60 g), sodium hydroxide (9.90 g), 40% benzyltrimethylammonium hydroxide in methanol (34.50 g) and 3-methyl-3-chlorobutyne (25.50 g) were stirred in water (150 ml) and dichloromethane (150 ml) for 5.5 days at room temperature. After separation of the layers, the aqueous layer was extracted twice with chloroform, and the combined organic phase evaporated leaving a gum which was taken up in ether and washed three times with 10% sodium hydroxide solution and with water before drying over magnesium sulphate. Removal of drying agent and solvent gave a viscous liquid having absorptions in the IR (film) at 2100, 2220, 3290 cm$^{-1}$. This liquid (20.91 g) was heated in o-dichlorobenzene (40 ml) at reflux temperature for 1.5 hours under nitrogen. After distillation of the solvent the fraction boiling at 110°-114°/0.02 mmHg (16.57 g) was collected, which on standing formed a low melting solid, having an IR absorption at 2230 cm$^{-1}$. (see M. Harfenist and E. Thom, J. Org. Chem., 37 841 (1972) who quote m.p. 36°-37°).

Addition to this 6-cyanochromene (16.50 g) dissolved in dimethyl sulphoxide (15 ml) containing water (3.24 ml), of N-bromosuccinimide (31.90 g) with vigorous stirring and cooling, followed by dilution with water and extraction with ethyl acetate gave a mixture which was boiled in acetone (300 ml) and water (100 ml) for 5 hours to hydrolyse the small amount of 3,4-dibromide present. Evaporation of solvents gave 2,2-dimethyl-3-bromo-6-cyano-3-4-dihydro-2H-benzo[b]pyran-4-ol as white crystals (24.37 g). A small sample had m.p. 128°-128.5° from 60°-80° petroleum ether, nmr (CDCl$_3$) δ 1.43 (3H), 1.62 (3H), 7.48 (1H, exchangeable) 4.07 (1H, d, J=9) 4.87 (1H, d, J=9), 6.80 (1H, d, J=8), 7.43 (1H, q, J=8,2), 7.78 (1H, d, J=2). Anal. Calcd. for C$_{12}$H$_{12}$NO$_2$Br: C, 51.07; H, 4.26; N, 4.96; Br, 28.37. Found: C, 50.95; H, 4.38; N, 5.03; Br, 28.39%.

The bromohydrin (24.30 g) was stirred with sodium hydroxide pellets (5.00 g) in water (250 ml) and dioxan (200 ml) for 3 hours at room temperature. The solvents were removed by distillation under high vacuum and the residue taken up in ether and washed with water and brine before drying over magnesium sulphate. Removal of drying agent and solvent and gave crude 2,2-dimethyl-3-4-epoxy-6-cyano-3-4-dihydro-2H-benzo[b]pyran: (16.02 g) as a gum, having an absorption at 2230 cm$^{-1}$ in the IR and Nmr (CCl$_4$) δ 1.26 (3H), 1.54 (3H), 3.40 and 3.80 (each 1H, d, J=4), 6.77 (1H, d, J=8), 7.43 (1H, q, J=8, 2), 7.58 (1H, d, J=2).

This epoxide (16.00 g) and pyrrolidine (7.20 ml) were refluxed in ethanol (240 ml) for 3.5 hours. Removal of solvent, addition of ethyl acetate, and washing with water was followed by extraction with 5 N hydrochloric acid. The acidic extract was basified with 10 N sodium hydroxide solution and extraction with ethyl acetate gave a gum which was taken up in diethyl ether containing a little ethanol and treated with ethereal hydrogen chloride. The precipitate was collected and washed with diethyl ether leaving trans-2,2-dimethyl-4-pyrrolidino-6-cyano-3,4-dihydro-2H-benzo[b]pyran-3-ol-hydrochloride as a white solid (11.02 g), m.p. 202°-204°; IR absorption at 2220 cm$^{-1}$; nmr (CDCl$_3$) δ 1.19 (3H), 1.73 (3H), 2.22 (4H, broad m), 3.13 (2H, broad m), 3.97 (2H, broad m), 4.20, (1H, d, J=8), 4.86 (1H, d, J=8), 5.58 (s, 1 exchangeable H, broad), 6.87 (1H, d, J=8), 7.47 (1H, q, J=8, 2), 8.72 (1H, d, J=2). Anal. Calcd. for C$_{16}$H$_{21}$N$_2$O$_2$Cl: C, 62.23; H, 6.86; N,9.07; Cl, 11.48, Found: C,62,34; H, 6.73; N,8.82; Cl, 11.40%.

EXAMPLE 4

Trans-2,2-dimethyl-3-(2,2-dimethylpropanoyloxy)-4-pyrrolidino-6-cyano-3,4-dihydro-2H-benzo[b]pyran To a solution of 4-dimethylaminopyridine (0.98 g) in dichloromethane (50 ml) was added 2,2-dimethylpropanoyl chloride (0.69 ml) dropwise and with gentle stirring, followed by crude trans-2,2-dimethyl-4-pyrrolidino-6-cyano-3,4-dihydro-2H-benzo[b]-pyran-3-ol (2.50 g) in dichloromethane (50 ml) during 4 minutes. The resulting red solution was heated under reflux for 40 hours before cooling and evaporation of solvent. The orange residue was taken up in ethyl acetate and washed with water, dried and evaporated leaving a mustard coloured solid (2.97 g) which was separated by chromatography on silica gel (110 g) with mixtures of ethyl acetate and 60°-80° petroleum ether using a gradient elution technique, into crude ester (1.12 g) and starting material (1.13 g). Recrystallization of the crude material from 60°-80° petroleum ether gave trans-2,2-dimethyl-3-(2,2-dimethylpropanoyloxy)-4 pyrrolidino-6-cyano-3,4-dihydro-2H-benzo[b]pyran (0.73 g) as white crystals of m.p. 109°-110° C.; IR absorptions at 1730, 2220 cm$^{-1}$; nmr (CDCl$_3$) δ 1.24 (9H), 1.29 (3H), 1.41 (3H), 1.75 (4H, broad m), 2.73 (4H, broad m), 4.09 (1H, d, J=9), 5.33 (1H, d, J=9), 6.86 (1H, d, J=8), 7.43 (1H, q, J=8, 2), 7.74 (1H, d, J=2). Anal. Calcd. for C$_{21}$H$_{28}$N$_2$O$_3$: C, 70.76; H, 7.92; N,7.86. Found: C, 70.74; H, 8.03, N, 7.76%.

EXAMPLE 5

Trans-2,2-dimethyl-3-methoxy-4-pyrrolidino-6-cyano-3,4-dihydro-2H-benzo[b]pyran To potassium t-butoxide (1.03 g) in dry toluene (40 ml) was added dropwise with stirring trans-2,2-dimethyl-4-pyrrolidino-6-cyano-3,4-dihydro-2H-benzo[b]pyran-3-ol (2.50 g) in toluene (100 ml) under nitrogen. After 10 minutes, methyl iodide (0.62 ml) in toluene (20 ml) was added dropwise, and the resulting yellow reaction mixture was stirred at 75°–80° C. for 16 hours. Cooling, and cautious addition of water, separation of the organic layer, washing with water, drying and evaporation gave a red gum (2.66 g) which was separated, by column chromatography on silica gel (110 g) with mixtures of ethyl acetate and 60°–80° petroleum ether using a gradient elution technique, into crude ether (1.34 g) and starting material (0.91 g). One crystallization from 60°–80° petroleum ether gave trans-2,2-dimethyl-3-methoxy-4-pyrrolidino-6-cyano-3,4-dihydro-2H-benzo[b]pyran (1.06 g) as off-white crystals m.p. 108°–109° C.; nmr (CDCl$_3$) δ 1.22 (3H), 1.50 (3H), 1.80 (4H, broad m), 2.76 (4H, broad m), 3.39 (1H, d, J=9), 3.51 (3H), 3.98 (1H, D, J=9), 6.76 (1H, d, J=8), 7.34 (1H, q, J=8, 2), 7.72 (1H, d, J=2). Anal. Calcd. for $C_{17}H_{22}N_2O_2$: C, 71.30; H, 7.74; N, 9.78. Found: C, 71.12; H, 7.96; N, 9.72%.

EXAMPLE 6

Resolution of trans-2,2-dimethyl-4-pyrrolidino-6-cyano-3,4-dihydro-2H-benzo[b]pyran-3-ol Racemic trans-2,2-dimethyl-4-pyrrolidino-6-cyano-3,4-dihydro-2H-benzo[b]pyran-3-ol (4.12 g) and (+)-tartaric acid (2.55 g), both dissolved in ethanol, were combined and the resulting solution evaporated leaving a cream foam. Three recrystallizations from ethanol gave a tartrate (1.01 g) of mp 173°–173.5° and an $[\alpha]_{water}^D = -64°$. Basification with NaHCO$_3$ and extraction with diethyl ether gave the minus isomer of the free base (0.64 g) of $[\alpha]_{EtOH}^D = -101°$. Treatment of an ethereal solution of this base base with ethereal-anhydrous HCl and one recrystallisation from ethanol-diethyl ether gave (−)-trans-2,2dimethyl-4-pyrrolidino-6-cyano-3,4-dihydro-2H-benzo-[b]-pyran-3-ol hydrochloride (0.49 g) of m.p. 184°–185° C., $[\alpha]_{water}^D = -98°$. Anal. Calcd. for $C_{16}H_{21}N_2O_2Cl$: C, 62.23; H, 6.85; N, 9.07; Cl, 11.48. Found: C, 62.29; H, 7.11; N, 9.17; Cl, 11.39%.

The mother liquors remaining after the three recrystallizations of the tartrate prepared from the racemic free base and (+)-tartaric acid were evaporated to dryness, dissolved in water, and rendered basic with sodium bicarbonate. Extraction with diethyl ether gave crude free base (3.10 g) which was treated with (−)-tartaric acid (1.67 g) in ethanol. Evaporation gave a cream foam (4.78 g).

Four recrystallizations from ethanol gave a tartrate (1.42 g) of mp 172.5°–173.5° and $[\alpha]_{water}^D + 58°$. Treatment with sodium bicarbonate and extraction with diethyl ether gave the plus isomer of the free base (0.88 g) of $[\alpha]_{EtOH}^D = +115°$. Treatment of an ethereal solution of this free base with ethereal anhydrous hydrogen chloride and one recrystallization from ethanol-diethyl ether gave (+)-trans-2,2-dimethyl-4-pyrrolidino-6-cyano-3,4-dihydro-2H-benzo[b]pyran-3-ol hydrochloride (0.87 g) of mp 175°–177° C., $[\alpha]_{water}^D = +100°$. Anal. Calcd. for $C_{16}H_{21}N_2O_2Cl$: C, 62.23; H, 6.85; N, 9.07; Cl, 11.48. Found: C, 61.94; H, 7.06; N, 9.28; Cl, 11.63%.

EXAMPLE 7

Trans-2,2-dimethyl-4-pyrrolidino-6-cyano-3,4-dihydro-2H-benzo[b]pyran-3-ol-hydrochloride Trans-2,2-dimethyl-3-bromo-3,4-dihydro-2H-benzo[b]pyran-4-ol (1.57 g) was dissolved in pyrrolidine (2.0 ml) and the solution heated under reflux for 25 min. After cooling, the solution was subjected to reduced pressure to remove traces of pyrrolidine. The residual gum was dissolved in ethyl acetate and washed with aqueous sodium carbonate solution and water before extraction with 1 N hydrochloric acid. The organic layer was discarded, and the aqueous layer was basified with 2.5 N sodium hydroxide and extracted with ethyl acetate. Water washing, drying, and evaporation of the organic layer gave the crude trans-2,2-dimethyl-4-pyrrolidino-6-cyano-3,4-dihydro-2H-benzo[b]pyran-3-ol (0.85 g) having identical chromatographic characteristics to that described in Example 3.

EXAMPLE 8

Trans-2,2-dimethyl-4-pyrrolidino-6-cyano-3,4-dihydro-2H-benzo[b]pyran-3-ol hydrochloride, magnesium stearate and microcrystalline cellulose are blended together and passed through a 40 mesh sieve (UK). The mixture is tabletted on a conventional rotary machine to produce a batch of 5000 tablets of the following:

| | |
|---|---|
| Magnesium stearate: | 0.2 mg |
| Active compound: | 10 mg |
| Microcrystalline cellulose: | 9.8 mg |

EXAMPLE 9

Trans-2,2-dimethyl-4-pyrrolidino-6-cyano-3,4-dihydro-2H-benzo[b]pyran-3-ol hydrochloride, sodium lauryl sulphate, lactose and sodium starch glycollate are blended together and passed through a 40 mesh sieve (UK). The mixture is tabletted on a conventional rotary machine to produce a batch of 5000 tablets of the following composition:

| | |
|---|---|
| Active compound: | 5 mg |
| Magnesium lauryl sulphate: | 0.1 mg |
| Lactose: | 103 mg |
| Sodium starch glycollate: | 1.9 mg |

What is claimed is:

1. A compound selected from the group consisting of benzo[b]pyran of the formula:

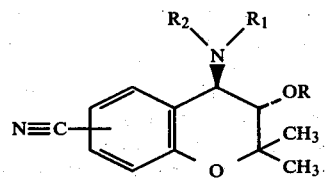

and the pharmaceutically acceptable acid addition salts thereof wherein R is hydrogen, alkyl of 1 to 3 carbon atoms, alkanoyl of up to 8 carbon atoms or benzoyl, $NR_1R_2$ is pyrrolidino, and the depicted cyano group is the 6-position.

2. A compound according to claim 1 wherein R is hydrogen.

3. The compound which is trans-2,2-dimethyl-4-pyrrolidino-6-cyano-3,4-dihydro-2H-benzo[b]pyran-3-ol or its hydrochloride salt.

4. The compound according to claim 3 which is the hydrochloride salt.

5. The compound according to claim 3 which is the (+) isomer.

6. The compound according to claim 5 which is the hydrochloride salt.

7. A pharmaceutical composition which comprises an anti-hypertensively effective amount of a compound according to claim 1 and a pharmaceutically acceptable carrier therefor.

8. A pharmaceutical composition which comprises an anti-hypertensively effective amount of trans-2,2-dimethyl-4-pyrrolidino-6-cyano-3,4-dihydro-2H-benzo[b]pyran-3-ol or a pharmaceutically acceptable salt thereof and a pharmaceutically acceptable carrier.

9. A composition according to claim 8 wherein the compound is (+)-trans-2,2-dimethyl-4-pyrrolidino-6-cyano-3,4-dihydro-2H-benzo[b]pyran-3-ol or a pharmaceutically acceptable salt thereof.

10. A composition according to claim 8 in orally administrable form and containing from about 1 to about 100 mg of said compound.

11. A composition according to claim 10 which contains from 2 to 50 mg. of said compound.

12. A composition according to claim 10 which contains from 5 to 25 mg. of said compound.

13. A method of treating hypertension in a human which comprises administering thereto an effective amount of a compound according to claim 1.

14. A method of treating hypertension in a human which comprises administering an effective amount of a compound according to claim 5.

* * * * *